United States Patent
Sieben-Xu et al.

(10) Patent No.: US 8,634,078 B2
(45) Date of Patent: Jan. 21, 2014

(54) SENSOR, METHOD FOR DETECTING THE PRESENCE AND/OR CONCENTRATION OF AN ANALYTE USING THE SENSOR, AND USE OF THE METHOD

(75) Inventors: Ling Sieben-Xu, Eindhoven (NL); Peter Offermans, Eindhoven (NL); Devrez Mehmet Karabacak, Eindhoven (NL); Mercedes Crego Calama, Geldrop-Mierlo (NL); Sywert Brongersma, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 70 days.

(21) Appl. No.: 13/239,023

(22) Filed: Sep. 21, 2011

(65) Prior Publication Data

US 2012/0075634 A1 Mar. 29, 2012

Related U.S. Application Data

(60) Provisional application No. 61/386,730, filed on Sep. 27, 2010.

(51) Int. Cl.
*G01N 21/55* (2006.01)
*B82Y 15/00* (2011.01)

(52) U.S. Cl.
USPC ............................ 356/445; 977/834; 977/773

(58) Field of Classification Search
USPC ............ 345/445, 72–73, 301; 372/45, 46, 50; 977/773, 834
See application file for complete search history.

(56) References Cited

U.S. PATENT DOCUMENTS 5,574,738 A * 11/1996 Morgan .......................... 372/28
5,712,865 A * 1/1998 Chow et al. .................... 372/96
5,879,961 A * 3/1999 Scott .............................. 438/32

(Continued)

FOREIGN PATENT DOCUMENTS

JP 2005308658 11/2005
WO 2009/070665 6/2009

OTHER PUBLICATIONS

Bora et al., "Near field detector for integrated surface plasmon resonance biosensor applications," Optics Express, vol. 17, No. 1, pp. 329-336 (Jan. 5, 2009).

(Continued)

*Primary Examiner* — Sang Nguyen
(74) *Attorney, Agent, or Firm* — McDonnell Boehnen Hulbert & Berghoff LLP

(57) ABSTRACT

Methods and sensors for detecting the presence and/or concentration of an analyte are disclosed. In one aspect, a sensing element for use in a sensor is disclosed. The sensing element comprises a resonant cavity device configured to emit optical radiation at an initial power level, a sensing layer exhibiting an initial refractive index, and a detector. The sensing layer is configured to absorb or adsorb an analyte and, in response to absorbing or adsorbing the analyte, exhibit a modified refractive index that differs from the initial refractive index. The resonant cavity device is further configured to, in response to the sensing layer absorbing or adsorbing the analyte, emit optical radiation at a modified power level based on the modified refractive index. The detector is configured to detect the modified power level.

22 Claims, 5 Drawing Sheets

(56) References Cited

U.S. PATENT DOCUMENTS

| | | | |
|---|---|---|---|
| 6,424,418 B2 | 7/2002 | Kawabata et al. | |
| 6,643,305 B2 * | 11/2003 | Bewley et al. | 372/45.01 |
| 6,678,300 B2 * | 1/2004 | Johnson et al. | 372/46.01 |
| 6,785,320 B1 | 8/2004 | Amos et al. | |
| 6,826,223 B1 * | 11/2004 | Meyer et al. | 372/96 |
| 7,177,021 B2 * | 2/2007 | Wang et al. | 356/301 |
| 7,356,057 B2 * | 4/2008 | Deng et al. | 372/34 |
| 7,359,048 B2 * | 4/2008 | Wang et al. | 356/301 |
| 7,604,981 B1 | 10/2009 | Harris, Jr. et al. | |
| 7,772,615 B2 * | 8/2010 | Ledentsov et al. | 257/184 |
| 2005/0041714 A1 | 2/2005 | Kim | |
| 2006/0077382 A1 | 4/2006 | Wang et al. | |

OTHER PUBLICATIONS

Levi et al., "Integrated semiconductor optical sensors for cellular and neural imaging," Applied Optics, vol. 46, No. 10, pp. 1881-1889 (Apr. 1, 2007).

European Search Report for Application No. EP 11 17 9667 mailed Jan. 20, 2012 (8 pages).

Guerrini et al., "Nanosensors Based on Viologen Functionalized Silver Nanoparticles: Few Molecules Surface-Enhanced Raman Spectroscopy Detection of Polycyclic Aromatic Hydrocarbons in Interparticle Hot Spots," Anaylitical Chemistry, vol. 81, No. 4, pp. 1418-1425 (Feb. 15, 2009).

\* cited by examiner

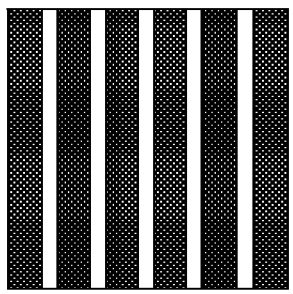
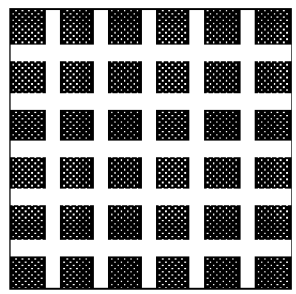
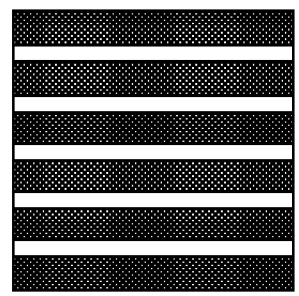
FIG. 3A          FIG. 3B          FIG. 3C
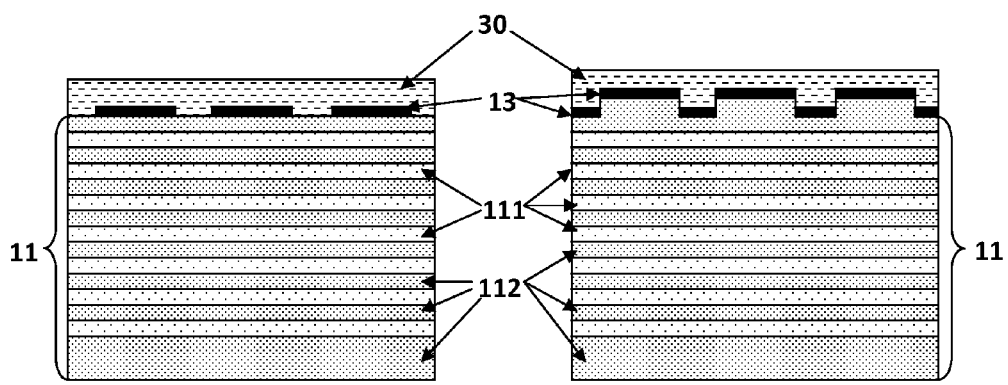
FIG. 4A          FIG. 4B

SENSOR, METHOD FOR DETECTING THE PRESENCE AND/OR CONCENTRATION OF AN ANALYTE USING THE SENSOR, AND USE OF THE METHOD

CROSS-REFERENCE TO RELATED APPLICATION

This application is a nonprovisional of U.S. Provisional Patent Application Ser. No. 61/386,730 filed Sep. 27, 2010, the contents of which are hereby incorporated by reference.

BACKGROUND

Surface Plasmon Polaritons (SPP) or Surface Plasmons are electromagnetic waves that can propagate along the interface between two media, such as at the interface between a metal and a dielectric material. They correspond to oscillations of electrons at the interface between the materials, such as those of electrons excited by photons. Surface plasmon resonance can be observed by measuring the reflectivity of p-polarized light of a given wavelength at a metal-dielectric interface for a varying angle of incidence. Alternatively, surface plasmon resonance can be observed by measuring the reflectivity of p-polarized light for a given angle of incidence at a metal-dielectric interface and a wavelength of the p-polarized light can be varied.

Surface plasmons present at the interface between, for example, a metal and a dielectric layer may be very sensitive to refractive index changes at the interface. The principle of surface-plasmon-resonance-based chemical sensing involves providing a thin layer of chemically active material, which may be called a sensing layer, on the metal surface at which the surface plasmons are excited. The excitation of the surface plasmon resonance is directly related to the interface properties. Changes in the sensing layer brought about by the presence of an analyte result in changes in the excitation angle or resonant wavelength of the surface plasmon resonance. By monitoring the excitation angle or the resonant wavelength, an analyte concentration may be determined.

The working principle of a surface-plasmon-resonance-based sensor can, for example, be based on the incident angle dependence of the surface plasmon resonance. Such an approach requires a prism coupler and may require rotatable equipment to obtain a larger range of incident angles. However, this type of sensor involving alignment and discrete components is not suitable for cheap mass production. Further, such sensors may suffer from the influence of vibrations due to the use of discrete components such as micro-objective lenses, lasers and photodetectors.

Another approach is wavelength spectroscopy surface plasmon resonance, in which a resonant wavelength shift of surface plasmon resonance is monitored. In this approach the need for a prism is avoided, and the size of the sensor can be smaller However, it requires a multi-wavelength source and a spectrometer, which can be expensive.

Surface plasmon resonance has been applied to different sensor applications such as, for example, for label-free sensing in biochemistry applications. However, commercially available surface plasmon resonance sensors are large in size, costly, not suitable for real-time monitoring, and require trained personnel to carry out the bio-analysis. By comparison, real-time monitoring with optical sensors involves smaller size sensors using lower cost transducers and lower power consumption.

In U.S. Pat. No. 6,424,418, Kawabata proposes a surface plasmon resonance sensor comprising a Vertical Cavity Surface Emitting Laser (VCSEL) and a Charge Coupled Device (CCD) array built on a common substrate. A cylindrical lens is provided above the laser to expand the laser light, and a thin metal film is provided for reflecting the laser light towards the CCD array. When light is emitted from the laser and impinges on the metal film, surface plasmon resonance can be induced at an incident angle which satisfies the surface plasmon resonance excitation condition. The surface emitting laser, metal film and CCD array are positioned such that the change in intensity of light reflected by the thin metal film, caused by the surface plasmon resonance, can be measured by the CCD array. However, the sensor is relatively large. Moreover, the technology involved requires integration between a Silicon CCD and VCSEL III-V material. As a single sensor has a limited measurement range, a VCSEL array and a two-dimensional CCD array may be needed.

In Japanese Patent Application Pub. No. JP 2005 308658, Takaaki discloses a compact and low cost surface plasmon resonance sensor. A VCSEL is used as a light source, and a sensor part is provided at the light-emitting surface of the VCSEL, the sensor part comprising a dielectric layer having an upper surface with a grating made by concentric recessions and protrusions. A metal film is provided on the surface of the dielectric layer, and receptors are fixed to the surface of the metal film. The metal film has an opening at its center part and an optical fiber probe is provided in the vicinity of the opening to detect leaking near-field light. In the absence of an analyte, surface plasmon resonance occurs in the sensor part, and facilitates the transmission of light through the central opening of the metal structure. Upon adsorption of the analyte, surface plasmon resonance no longer exists in the sensor part, and the intensity of the leaking light changes. This change in intensity of the transmitted power is detected by means of the optical fiber probe. In this approach, however, external detection (e.g., using the optical fiber probe) is needed, requiring additional alignment. Further, there exists a trade-off between the sensor sensitivity and the optical power transmission. A higher power transmission can be obtained with a larger central opening in the metal structure, but this leads to a broader spectral width, which limits the sensor sensitivity. On the other hand, a narrower spectral width and thus a higher sensitivity can be obtained with a smaller central opening, but this results in a very low optical power transmission.

SUMMARY

Disclosed is an optical sensor based on surface plasmon resonance. Also disclosed is a method for measuring the presence and/or the concentration of an analyte using such an optical sensor.

The disclosed sensor is can be used for real-time monitoring. Further, the disclosed sensor can be small (for example, having a size on the order of 20 µm×20 µm) and can have low power consumption (for example, in the nanowatt range). Still further, the disclosed sensor can be low cost and have a high sensitivity.

In one aspect, a sensor is disclosed that comprises at least one sensing element. The at least one sensing element comprises a resonant cavity device for emitting optical radiation at an operation wavelength. The resonant cavity device, in turn, comprises a first mirror at a first side and a second mirror at a second side opposite to the first side. The second mirror comprises a structured layer supporting SPR. The at least one sensing element further comprises a sensing layer overlaying the structured layer of the second mirror. The sensing layer is configured for exposure to an analyte and has a refractive index that changes upon absorption or adsorption of the analyte, resulting in a change of power of the optical radiation. The at least one sensing element further includes a detection component configured to detect the change of power of the optical radiation. The detection component may be integrated with the resonant cavity device, or may be located at the side of the structured layer. The disclosed optical sensor may be fully integrated, such that no alignment after fabrication is necessary.

In some embodiments, the resonant cavity device may comprise a laser, The resonant cavity device can for example be a laser, such as a Vertical Cavity Surface Emitting Laser (VCSEL). However, the present invention is not limited thereto and any suitable resonant cavity device known to a person skilled in the art can be used.

In some embodiments, the first side may be a radiation emitting side.

In some embodiments, the first side may comprise a second structured layer supporting surface plasmon resonance. Further, the at least one sensing element may further comprise a second sensing layer overlaying the first mirror and provided over the second structured layer, the second sensing layer being provided for exposure to an analyte and having a refractive index which changes upon absorption or adsorption of the analyte, resulting in a change of power of the optical radiation. Such a second structured layer and second sensing layer, similar to the first structured layer and first second sensing layer applied to the second side, allows for an improved detection of a single analyte, together with the first sensing layer and first structured layer at the second side, or detection of a further analyte different from the analyte detected at the first side.

In some embodiments, the first mirror of the resonant cavity device may be a III-V Distributed Bragg Reflector (DBR) mirror.

In some embodiments, the second mirror may comprise at least one and/or several periods of a dielectric DBR mirror combined with a structured metal layer, providing a reflectivity of more than 99%, or even more than 99.5%, in a wavelength range comprising the operation wavelength. The structured metal layer can comprise a metal grating, a metal nanohole array, and/or metal nanoparticles which can support surface plasmon resonance.

Alternately or additionally, the second mirror may comprise at least one and/or several periods of a DBR mirror comprising non-dielectric materials that are transparent to the operation wavelength (e.g., the lasing wavelength), and the structured layer may be different from a metal layer that can support surface plasmon resonance.

The sensing layer is provided on or over the second mirror (e.g., over the metal layer) for absorbing or adsorbing an analyte or a target material to be detected. The sensing layer can be any layer that changes its refractive index upon exposure to an analyte. It can, for example, comprise bio-molecules, a polymer or binding-DNA.

In operation, an electrical current is injected into the resonant cavity device (e.g., through metal contacts of the resonant cavity device) such that the resonant cavity device emits optical radiation at a first output optical power. Upon absorption or adsorption of an analyte in or on the sensing layer, the refractive index of the sensing layer changes, thereby resulting in excitation of a surface plasmon resonance at the interface between the structured layer (e.g., a metal layer) and the sensing layer. The excitation of the surface plasmon resonance may result in a reduction of the reflectivity of the second mirror (e.g., to less than 97% or less than 95%).

The change of the refractive index of the sensing layer leads to a change (e.g., a reduction) of the output optical power of the resonant cavity device. The changes in the optical power emitted by the resonant cavity device are detected by the detection component of the sensing element. The detection component may comprise, for example, a photodetector (e.g., an integrated photodetector) and may be configured to detect the presence and/or the concentration level of a target material or analyte. In some embodiments, the photodetector may be configured to detect the optical power of the optical radiation emitted by the resonant cavity device.

The change of the reflectivity of the second mirror may also lead to a change in carrier density inside the resonant cavity, leading to a change of a junction voltage. Therefore the concentration level of an analyte can also be monitored by measuring a change in junction voltage.

In embodiments where the resonant cavity device is a laser such as, for example, a VCSEL, if the electrical current injected into the device is higher than a threshold current of the laser, the laser will start to lase.

In some embodiments, upon absorption or adsorption of an analyte, the refractive index of the sensing layer changes, resulting in, for example, excitation of a surface plasmon resonance at the interface between the structured, preferably metal, layer and the sensing layer and, in turn, a reduction of the reflectivity of the second mirror, e.g., to less than 97% or less than 95%. The reduction of the reflectivity of the second mirror leads to a reduction of the output optical power of, for example, the VCSEL. In some cases, the VCSEL may even stop lasing. The changes in the optical power emitted by the VCSEL are detected by the detection component (e.g., by the photodetector) and are a measure for the presence and/or the concentration level of a target material.

In some embodiments, reduction of the reflectivity of the second mirror may lead to a change in carrier density inside the resonant cavity, leading to a change of a junction voltage. Therefore the concentration level of an analyte can also be monitored by measuring a change in junction voltage by for example means for measuring the change in junction voltage.

In the disclosed sensor, the resonant cavity device (e.g., the VCSEL) may act both as a light source and as a sensing element. The second mirror, for example, comprising a structured metal layer in combination with a dielectric DBR mirror, offers high reflectivity and in addition supports surface plasmon resonance. The detection component (e.g., the photodetector) monitors the output optical power changes of the resonant cavity device.

In another aspect, a method is disclosed. In some embodiments, the method may comprise injecting an electrical current higher than a threshold current into the resonant cavity device and detecting the optical power of the optical radiation emitted by the resonant cavity device. Changes in the optical power emitted by the resonant cavity device can be detected by the detection component and are a measure for the presence and/or the concentration level of a target material or analyte. The presence and/or concentration level of an analyte can also be monitored by measuring a change in junction voltage.

In some embodiments, injecting the electrical current can comprise injecting a continuous electrical current or it can comprise injecting a pulsed electrical current.

In some embodiments, the light source, the sensing layer and/or the detection component may be fully integrated, such that the need for alignment after fabrication is avoided. Full integration also offers a reduced sensitivity to vibrations.

The disclosed sensor may have a small size, such as, for example, less than 20 μm×20 μm. Other sizes are possible as well.

Further, the disclosed sensor may have low power consumption, such as, for example, in the mW range. In embodiments where injecting the electrical current comprises injecting a pulsed electrical current, short optical pulses (e.g., 1 microsecond) may be used to inject the pulsed electrical current, with a relatively long (e.g. 1 minute) stand-by period in between the pulses. In these embodiments, the power consumption may even be reduced to the nW range.

Still further, the disclosed sensor may have improved sensitivity as compared with typical sensors, in particular when the resonant cavity device comprises a laser. This is due to the exponential relation between the reflectivity and the output optical power, leading to a substantial optical power change even in case of a small reflectivity change.

The disclosed sensor may be used for detecting different analytes, such as gas, vapor, molecules, virus, DNA, and other analytes by implementing different sensing layers. If the sensing layer itself is not selective for different analytes, different materials for the sensing layer can be used for detecting different analytes.

In some embodiments, the disclosed sensor may comprise a plurality of sensing elements (e.g., an array of sensing elements) that may be used for multi-target sensing.

The disclosed sensor may be used for rapid detection and identification of chemical and biological species in different application fields, such as, for example, development of biotech products, medical diagnostics (hormones, antibodies, biomarkers, etc.), environmental monitoring (contaminants, pollutants, etc.), food safety (foodborne pathogens, toxins, etc.), and security (chemical and biological agents, etc.).

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. Further, it is understood that this summary is merely an example and is not intended to limit the scope of the invention as claimed. The invention, both as to organization and method of operation, together with features and advantages thereof, may best be understood by reference to the following detailed description when read in conjunction with the accompanying drawings.

BRIEF DESCRIPTION OF THE DRAWINGS

FIGS. 3A-3C show top views of some exemplary metal grating structures that can be used to support surface plasmon resonance at a second mirror of an example sensing element, in accordance with an embodiment.

FIGS. 4A-4B show two possible cross-sections of example second mirrors of a sensing element, in accordance with embodiments. FIG. 4A shows an embodiment in which a metal grating is formed on a flat dielectric layer surface, and FIG. 4B shows an embodiment in which a metal grating is formed on a structured dielectric layer surface.

Figure 1:
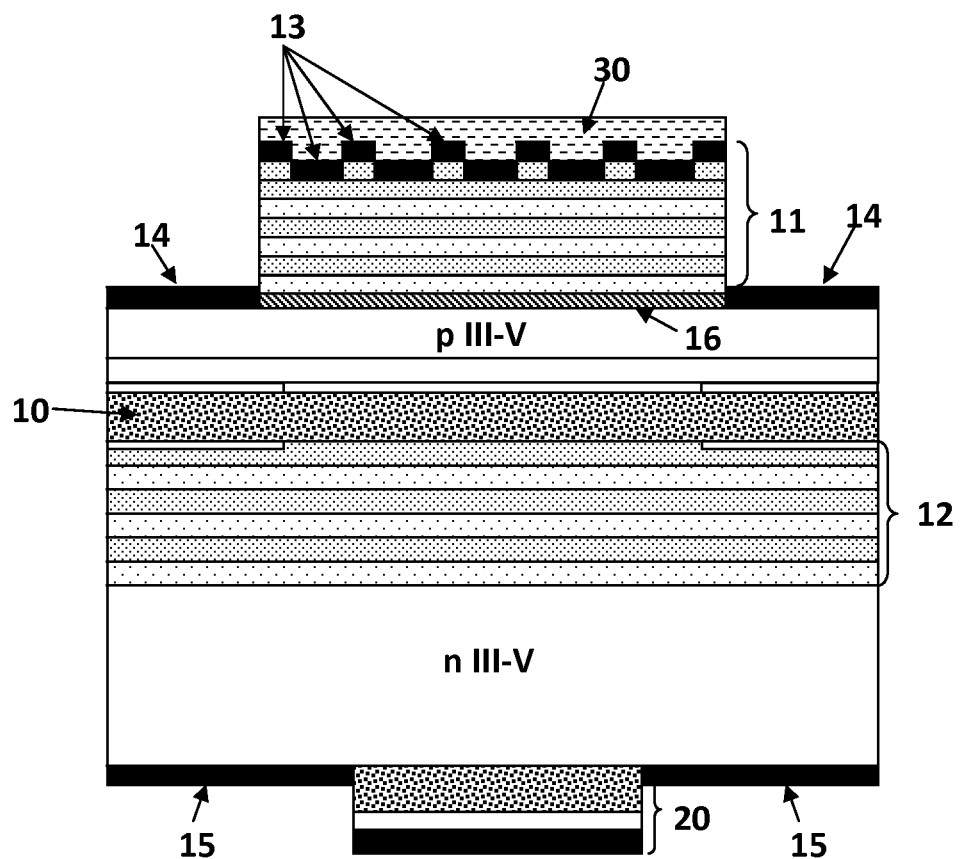
FIG. 1 schematically illustrates a cross-section of an example sensing element of a surface plasmon resonance sensor, in accordance with an embodiment.

Any reference signs in the claims shall not be construed as limiting the scope of the present invention. In the different drawings, the same reference signs refer to the same or analogous elements.

DETAILED DESCRIPTION

In the following detailed description, numerous specific details are set forth in order to provide a thorough understanding of the invention and how it may be practiced in particular embodiments. However, it will be understood that the present invention may be practiced without these specific details. In other instances, well-known methods, procedures and techniques have not been described in detail, so as not to obscure the present invention. While the present invention will be described with respect to particular embodiments and with reference to certain drawings, the invention is not limited hereto. The drawings included and described herein are schematic and are not limiting the scope of the invention. It is also noted that in the drawings, the size of some elements may be exaggerated and, therefore, not drawn to scale for illustrative purposes.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

A sensor according to the present invention comprises at least one sensing element, the at least one sensing element comprising a resonant cavity device for emitting optical radiation at an operation wavelength, the resonant cavity device comprising a first mirror at a first side (e.g., the radiation emitting side), and a second mirror at a second side opposite to the first side. The at least one sensing element further comprises a sensing layer overlaying the second mirror, and a detection component (e.g., a photodetector, such as an integrated photodetector) at the first side of the resonant cavity device, for detecting the optical power of the optical radiation emitted by the resonant cavity device.

The first mirror of the resonant cavity device can, for example, be a III-V DBR mirror comprising a plurality of layers with alternating high and low refractive indices.

The second mirror can, for example, comprise several periods of a dielectric DBR mirror combined with a structured layer, such as a structured metal layer. The structured metal layer can, for example, comprise a metal grating structure and/or can comprise metal nanoholes and/or can comprise metal nanoparticles which can support surface plasmon resonance. The metal nanoholes or metal nanoparticles can be arranged in an array, or in another configuration.

The sensing layer may be provided over or on the structured layer and can, for example, comprise a polymer, biomolecules or binding-DNA. The thickness of the sensing layer may depend on the analyte to be sensed. For example, the thickness of the sensing layer may be in the micrometer range when the analyte is vapor, or may be thinner than 1 micrometer if the analyte is a gas, or may in the order of a few hundreds of nanometers for the detection of biomolecules. Other examples are possible as well. In general, any suitable sensing layer thickness known to a person skilled in the art may be used.

In some embodiments, the sensing layer can be adjacent to the second mirror or an additional layer can be present between the sensing layer and the second mirror. This additional layer can, for example, be used to tune the refractive index of the environment near the metal structure, and thus the resonant SPR wavelength.

In some embodiments, the resonant cavity device may be a VCSEL, but the invention is not limited thereto. For example, in a sensor of the present invention the resonant cavity device can be a LED with roundtrip reflection, a Fabry-Perot cavity or any other suitable resonant cavity device known to a person skilled in the art.

A typical VCSEL may comprise a short active region in between two distributed Bragg reflector (DBR) mirrors with very high reflectivity (≥99%), the III-V DBR mirrors typically comprising tens of layers with alternating high and low refractive indices. The active region may comprise a III-V quantum well (QW) offering a high gain coefficient.

FIG. 1 schematically illustrates a cross-section of an example sensing element of a surface plasmon resonance sensor, in accordance with an embodiment. As shown, the sensor comprises an active region 10 in between two mirrors: a first mirror 12 at the light emitting side of the VCSEL and a second mirror 11 at a side opposite to the light emitting side of the VCSEL.

The second DBR dielectric mirror 11 may comprise, for example, 2 to 10 periods, e.g. 4 to 8 periods of alternating layers with high and low refractive indexes, and a structured metal layer 13, such as, for example, a metal grating or metal nanohole array or metal nano-particles, possibly offering higher than 99% of reflectivity.

An anti-reflection (AR) coating 16 can be provided at the III-V-dielectric interface for suppressing non-desired residual reflections. The AR coating can, for example, comprise a plurality of layers.

A sensing layer 30 for adsorbing or absorbing an environmental target or analyte (gas, molecules, virus, DNAs, etc.) is provided on the second mirror of the VCSEL. The sensing layer 30 can be any layer that changes its refractive index upon exposure to an analyte to be detected.

FIGS. 3A-3C show top views of some exemplary metal grating structures that can be used to support surface plasmon resonance at a second mirror of an example sensing element, in accordance with an embodiment. Different grating structures or orientations can be designed to match the polarization status of the VCSEL. For example, the structure shown in FIG. 3A can be used in case of p-polarization, the structure shown in FIG. 3B can be used in case of p- and s-polarization, and the structure shown in FIG. 3C can be used in case of s-polarization. However, the present invention is not limited thereto and any other suitable structured layer 13 known to a person skilled in the art can be used.

FIGS. 4A-4B show two possible cross-sections of example second mirrors 11 of a sensing element, in accordance with embodiments. FIG. 4A shows an embodiment in which a metal grating is formed on a flat dielectric layer surface, and FIG. 4B shows an embodiment in which a metal grating is formed on a structured dielectric layer surface. In the embodiments shown, the second mirror 11 comprises a dielectric DBR mirror (comprising alternating layers 111, 112 with higher refractive index and lower refractive index, respectively) combined with a structured layer 13.

In some embodiments, the sensor may comprise a photodetector 20, such as an integrated photodetector, at the light-emitting side of the VCSEL. The integrated photodetector can comprise a stack of layers (e.g., p-i-n). The integrated photodetector can be wafer-bonded or glued at the light-emitting side of the VCSEL, or it can be grown in a same process as the VCSEL, since the photodetector can possibly share the same III-V material with the VCSEL. The detection component, which may also be integrated, can be adjacent to the first mirror, or can be at predetermined distance from the first mirror.

In operation, an electrical current is injected through the p-type metal contacts 14 and the n-type metal contacts 15 of the VCSEL. When the injected electrical current is higher than a threshold current (for example several mA), the VCSEL starts to lase. When the refractive index of the sensing layer 30 changes due to the absorption or adsorption of a target material (gas, bio-liquid, virus, DNAs, etc.) and the surface plasmon resonance is excited near or at the operation wavelength, the reflectivity of the second mirror 11 decreases. Consequently, the threshold current for lasing increases, and the output optical power of the VCSEL drops for the same injection current. The changes in optical output power of the VCSEL are measured with the detection component 20.

Figure 2:
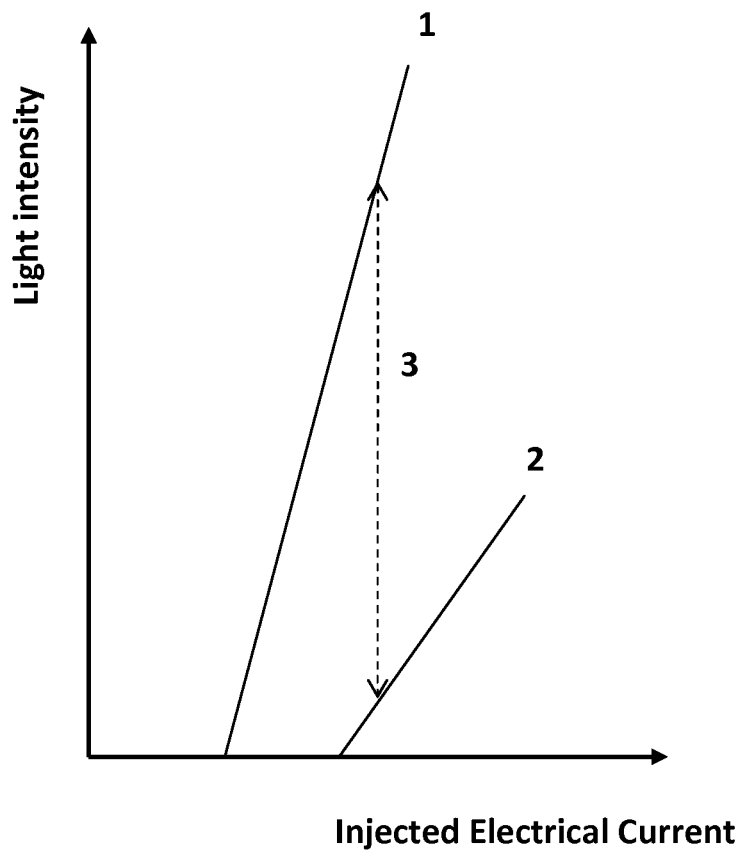
FIG. 2 schematically illustrates the intensity of the light emitted by a VCSEL (1) in the absence of an analyte, and (2) after absorption or adsorption of an analyte at the sensing layer, for an example sensor in accordance with an embodiment.

FIG. 2 schematically illustrates the intensity of the light emitted by a VCSEL (1) in the absence of an analyte, and (2) after absorption or adsorption of an analyte at the sensing layer, for an example sensor in accordance with an embodiment. The difference (3) between the optical power emitted by the VSCEL before and after exposure to a target material for a given injection current can be detected by the detection component.

In some embodiments, the structure can also be operated the other way around, namely the detection of the transition from non-lasing (curve 2) to lasing (curve 1) upon adsorption or absorption of a target material resulting in a power increase can be measured by the detection component.

In some embodiments, the VCSEL (or, more generally, the resonant cavity device) functions both as a light source and as a sensing element. Due to the preferred total integration, the sensing element and/or the sensor as a whole can be both compact and low cost. The optical power change is prominent as it is related to breaking or initiation of a lasing condition, thus leading to a higher sensitivity. In some embodiments, an array of sensing elements can be used for obtaining a larger measurement range.

To illustrate the working principle of the disclosed sensor, simulations were performed for a sensor as illustrated in FIG. 1. The simulated sensor comprises a VCSEL (GaAs substrate), the III/V first DBR mirror is composed of 15 periods of AlGaAs with different compositions, the active layer is a multi-quantum well with a gain peak at 860 nm, and the second mirror consists of a structured metal grating and six periods of alternating SiNx and SiO2.

In the simulations, the thickness of each SiNx layer and each SiO2 layer was 128 nm, and a gold metal grating with a period of 620 nm was assumed with a metal thickness of 50 nm and a 60 nm wide slit. The structure of the second mirror consisting of a dielectric DBR and metal grating can be seen in FIG. 4A. The sensing layer has an intrinsic refractive index of 1.3, which gradually increases with an increasing amount of analyte. This can, for example, be obtained by flowing a target liquid with a higher index over the sensing layer surface.

In the numerical simulations, the intensity of the radiation emitted by the laser (VCSEL) was analyzed as a function of the refractive index of the sensing layer, for a sensing element of the present invention.

Figure 5:
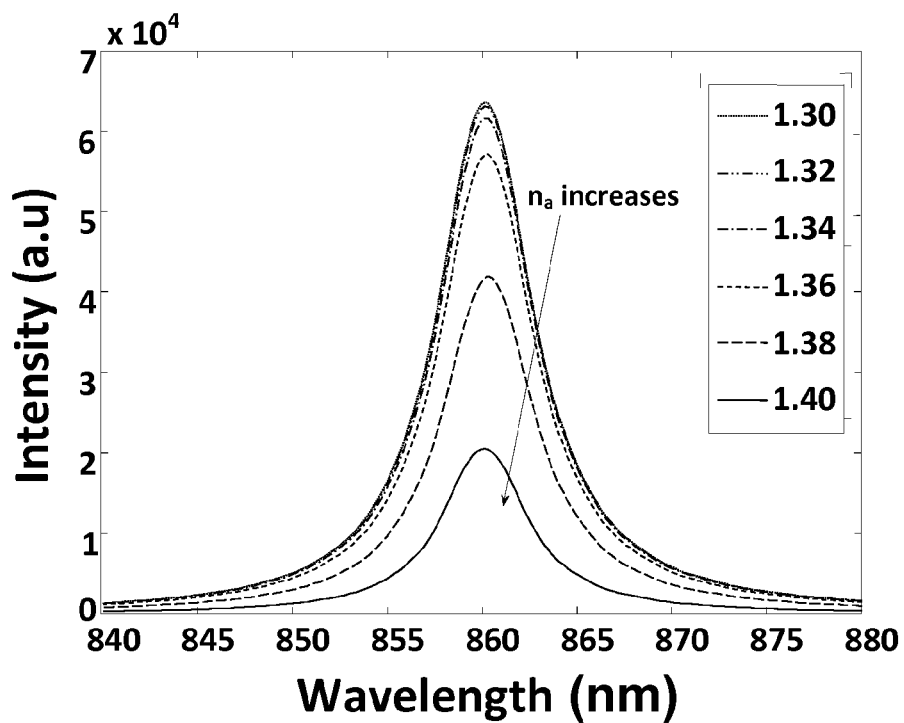
FIG. 5 shows simulated intensity change of an example sensor as a function of the wavelength for different values of the refractive index of the sensing layer, in accordance with an embodiment.

FIG. 5 shows simulated intensity change of an example sensor as a function of the wavelength for different values of the refractive index of the sensing layer, in accordance with an embodiment. From these results it can be concluded that the output power of the VCSEL at the peak wavelength (860 nm) of the sensing element decreases gradually from $6.5 \times 10^4$ to $1.8 \times 10^4$ when the refractive index of the sensing layer changes from 1.3 to 1.4, e.g. resulting from the presence of an analyte.

Figure 6:
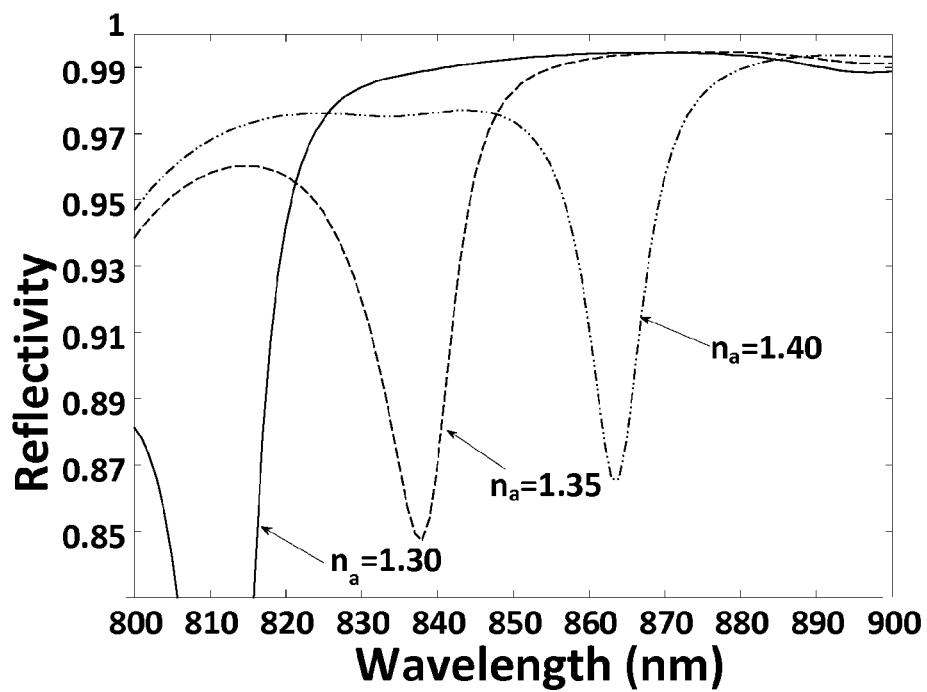
FIG. 6 shows simulated reflectivity of a second mirror of an example sensor as a function of the wavelength of incident light, in accordance with an embodiment.

FIG. 6 shows simulated reflectivity of a second mirror of an example sensor as a function of the wavelength of incident light, in accordance with an embodiment. As shown, the reflectivity of the second mirror changes from 99.3% to 86.6% at a wavelength of 863 nm when the refractive index of the sensing layer changes from 1.30 to 1.40, which corresponds to the output intensity change in FIG. 5.

Although in the examples describe above the operation wavelength used is close to 860 nm, the present disclosure is not limited thereto. The disclosed sensor can be designed for use at any other suitable wavelength. For example, the second mirror can be designed for obtaining a very high reflectivity at any wavelength by properly designing the dielectric DBR mirror and the metal grating. The thickness of the alternating dielectric layers depends on the target wavelength. In the context of the present disclosure, the thickness may be equal to the target wavelength or operating wavelength divided by 4n, wherein n is the effective refractive index of the dielectric materials.

Figure 7:
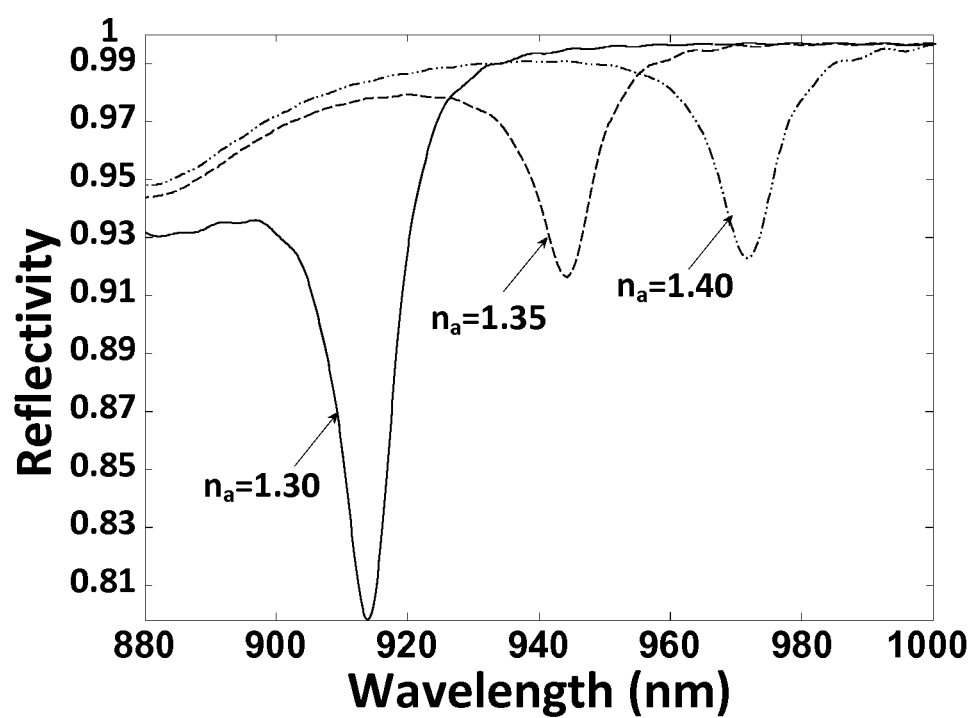
FIG. 7 shows simulated reflectivity of a second mirror of another example sensor as a function of the wavelength of incident light, in accordance with an embodiment.

FIG. 7 shows simulated reflectivity of a second mirror of another example sensor as a function of the wavelength of incident light, in accordance with an embodiment. In FIG. 7, second mirror is designed for maximum reflectivity at 970 nm. In the simulated structure, the thickness of the alternating SiNx and SiO2 layers was 145 nm, and the metal grating period was 700 nm. The reflectivity of the second mirror changes from 99.8% to 93% at a wavelength of 970 nm when the refractive index changes from 1.30 to 1.40.

The sensing layer material may be selected depending on the analyte to be detected. For example, the sensing layer material can comprise a polymer for detecting alcohol vapor, or an antibody for DNA analysis. Other examples are possible as well.

The metal supporting the surface plasmons can be, for example, silver or gold. Other examples are possible as well. The exact number of period pairs and the thickness of the metal layer of the second mirror are dependent on the operational wavelength and the target reflectivity and sensitivity.

The invention claimed is:

1. A sensing element comprising:
   a resonant cavity device configured to emit optical radiation at an initial power level;
   a sensing layer configured to support surface plasmon resonance that exhibits an initial refractive index; and
   a detector, wherein:
   the sensing layer is configured to absorb or adsorb an analyte and, in response to absorbing or adsorbing the analyte, exhibit a modified refractive index that differs from the initial refractive index;
   the resonant cavity device is further configured to, in response to the sensing layer absorbing or adsorbing the analyte, emit the optical radiation at a modified power level based on the modified refractive index; and
   the detector is configured to detect the modified power level of the optical radiation.

2. The sensing element of claim 1, wherein the resonant cavity device comprises:
   a first mirror on a first side of the resonant cavity device, wherein the first mirror is configured to emit the optical radiation; and
   a second mirror on a second side opposite the first side, wherein the second mirror exhibits an initial reflectivity.

3. The sensing element of claim 2, wherein, in response to the sensing layer absorbing or adsorbing the analyte, the second mirror exhibits a modified reflectivity that is lower than the initial reflectivity.

4. The sensor of claim 3, wherein the modified reflectivity is less than about 97%.

5. The sensor of claim 2, wherein the second mirror comprises a structured layer.

6. The sensor of claim 5, wherein the structured layer comprises a structured metal layer.

7. The sensor of claim 5, wherein the structured layer comprises at least one of a metal grating, a metal nanohole array, or a metal nanoparticle array.

8. The sensor of claim 2, wherein at least one of the first mirror and the second mirror comprises a distributed Bragg reflector (DBR) mirror.

9. The sensor of claim 8, wherein the second mirror comprises a DBR mirror integrated with the structured layer.

10. The sensor of claim 8, wherein the second mirror comprises a number of periods of a DBR mirror.

11. The sensor of claim 8, wherein the DBR mirror comprise a dielectric DBR mirror.

12. The sensor of claim 1, wherein the detector comprises a photodetector.

13. The sensor of claim 1, wherein the resonant cavity device comprises a vertical cavity surface emitting laser.

14. The sensor of claim 1, wherein the sensing layer comprises at least one of bio-molecules, polymers, or binding-DNA.

15. The sensor of claim 1, wherein the initial reflectivity is greater than about 99% in a predetermined wavelength range.

16. The sensor of claim 1, wherein, to detect the modified power level of the optical radiation, the detector is further configured to measure a change in a junction voltage inside the resonant cavity device.

17. A method comprising:
   using a first mirror in a resonant cavity device in a sensing element to emit optical radiation at an initial power level;

exposing a sensing layer in the sensing element that is configured to support surface plasmon resonance to an analyte, thereby reducing a reflectivity of a second mirror in the resonant cavity device;

in response to reducing the reflectivity of the sensing layer, using the first mirror of the resonant cavity device to emit the optical radiation at a modified power level; and using a detector in the sensing element to detect the modified power level of the optical radiation.

18. The method of claim 17, further comprising:

in response to exposing the sensing layer to the analyte, exciting a surface plasmon resonance between the sensing layer and the second mirror, thereby reducing the reflectivity of the second mirror.

19. The method of claim 17, wherein, in response to reducing the reflectivity of the sensing layer, the resonant cavity device exhibits a modified carrier density, thereby causing a change in a junction voltage of the resonant cavity device, wherein using the detector to detect the modified power level of the optical radiation comprises:

using the detector to detect the change in the junction voltage.

20. A sensor comprising:

a number of sensing elements, each sensing element comprising:

a resonant cavity device configured to emit optical radiation at an initial power level;

a sensing layer configured to support surface plasmon resonance that exhibits an initial refractive index; and a detector, wherein:

the sensing layer is configured to absorb or adsorb an analyte and, in response to absorbing or adsorbing the analyte, exhibit a modified refractive index that differs from the initial refractive index;

the resonant cavity device is further configured to, in response to the sensing layer absorbing or adsorbing the analyte, emit the optical radiation at a modified power level based on the modified refractive index; and the detector is configured to detect the modified power level of the optical radiation.

21. The sensor of claim 20, wherein the number of sensing elements comprises an array of sensing elements.

22. The sensor of claim 20, wherein, to detect the modified power level of the optical radiation, the detector is configured to detect one of the optical radiation emitted by the resonant cavity device or a change in a junction voltage inside the resonant cavity device.

* * * * *